(12) United States Patent
Smith et al.

(10) Patent No.: US 11,534,555 B2
(45) Date of Patent: Dec. 27, 2022

(54) ASSEMBLY FOR A MEDICATION DELIVERY DEVICE AND MEDICATION DELIVERY DEVICE COMPRISING SUCH AN ASSEMBLY

(71) Applicant: NORTON HEALTHCARE LIMITED, Castleford (GB)

(72) Inventors: Christopher James Smith, Prenton (GB); Dale Marc Comley, Parchwich (GB); Lee Thomas Smith, Tixall (GB)

(73) Assignee: NORTON HEALTHCARE LIMITED, Castleford (GB)

( * ) Notice: Subject to any disclaimer, the term of this patent is extended or adjusted under 35 U.S.C. 154(b) by 249 days.

(21) Appl. No.: 16/483,161

(22) PCT Filed: Jan. 25, 2018

(86) PCT No.: PCT/EP2018/051880
§ 371 (c)(1),
(2) Date: Aug. 2, 2019

(87) PCT Pub. No.: WO2018/141636
PCT Pub. Date: Aug. 9, 2018

(65) Prior Publication Data
US 2020/0001017 A1   Jan. 2, 2020

(30) Foreign Application Priority Data
Feb. 3, 2017 (EP) .................... 17154642

(51) Int. Cl.
*A61M 5/315* (2006.01)
*A61M 5/50* (2006.01)

(52) U.S. Cl.
CPC .... *A61M 5/31551* (2013.01); *A61M 5/31511* (2013.01); *A61M 5/31536* (2013.01); *A61M 2005/5033* (2013.01)

(58) Field of Classification Search
CPC .......... A61M 5/31551; A61M 5/31511; A61M 5/31536; A61M 5/31528; A61M 5/3146; A61M 5/31501; A61M 2005/5033
See application file for complete search history.

(56) References Cited

U.S. PATENT DOCUMENTS 5,226,895 A   7/1993  Harris
2006/0270985 A1   11/2006  Hommann et al.
(Continued)

FOREIGN PATENT DOCUMENTS

DE   102004045326 A1   11/2005
EP      0496141 A1    7/1992
(Continued)

*Primary Examiner* — Nathan R Price
*Assistant Examiner* — Justin L Zamory
(74) *Attorney, Agent, or Firm* — David S. Safran; Calderon Safran & Cole P.C.

(57) ABSTRACT

An assembly for a medication delivery device having a body, a piston rod and a setting nut. The piston rod is rotatable relative to the body in a dose setting state and is axially movable in a distal direction with respect to the body in a dose delivering state. The setting nut is secured against rotational movement with respect to the body, but is axially movable relative to the body, being helically coupled with the piston rod to axially travel in the proximal direction for setting a dose of a medication due to a helical movement of the setting nut with respect to the piston rod when the piston rod is rotated in the dose setting state, and is able to axially travel in the distal direction for delivering the set dose of the medication when the piston rod is axially moved in the dose delivering state of the assembly.

14 Claims, 9 Drawing Sheets

(56) References Cited

U.S. PATENT DOCUMENTS

| | | |
|---|---|---|
| 2007/0167921 A1 | 7/2007 | Burren et al. |
| 2009/0054846 A1 | 2/2009 | Moser et al. |
| 2010/0010454 A1* | 1/2010 | Marshall ............ A61M 5/2033 604/208 |
| 2012/0203184 A1 | 8/2012 | Selz et al. |
| 2012/0316508 A1 | 12/2012 | Kirchhofer |
| 2015/0250950 A1* | 9/2015 | Moser ............... A61M 5/31536 604/110 |
| 2016/0175528 A1 | 6/2016 | Marshall et al. |
| 2016/0367760 A1 | 12/2016 | Bainton et al. |

FOREIGN PATENT DOCUMENTS

| | | |
|---|---|---|
| WO | 9004423 A1 | 5/1990 |
| WO | 2011088894 A1 | 7/2011 |
| WO | 2012118687 A1 | 9/2012 |
| WO | 2016033701 A1 | 3/2016 |

\* cited by examiner

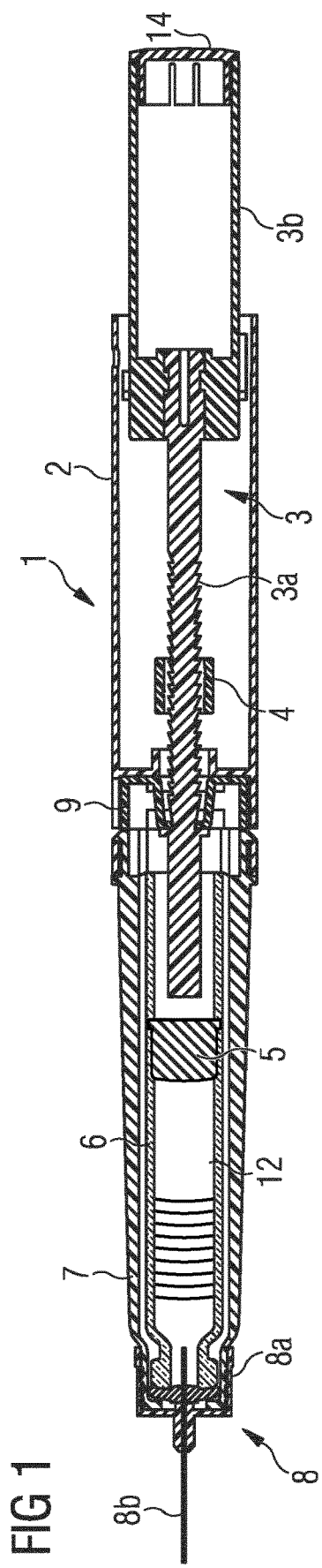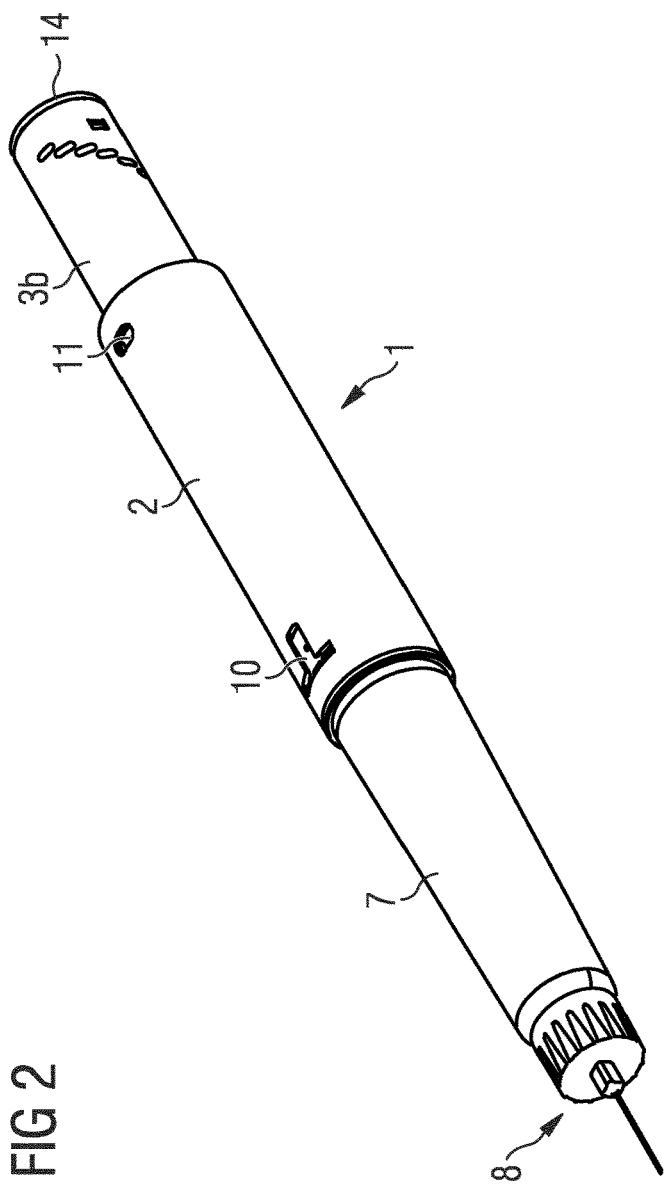

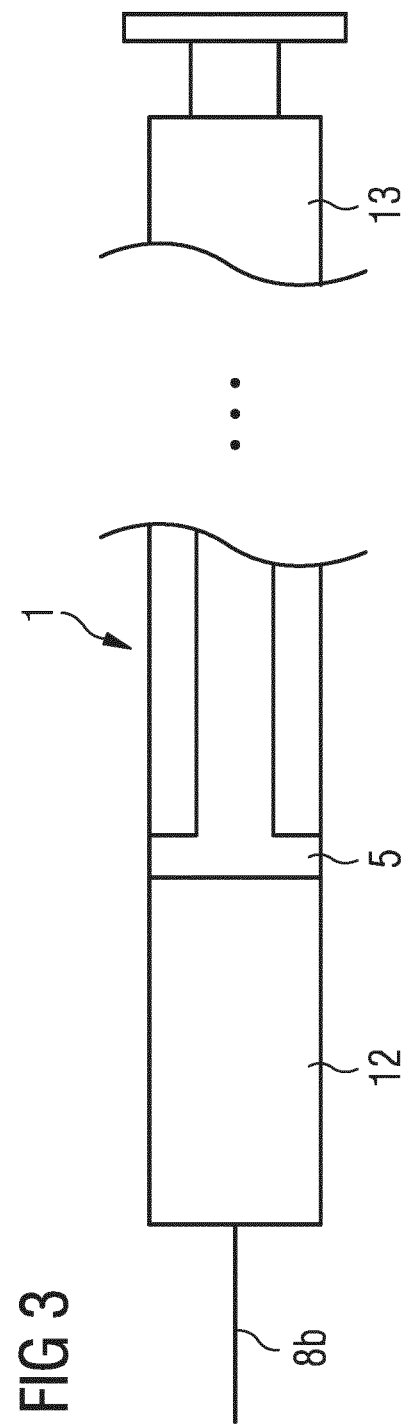

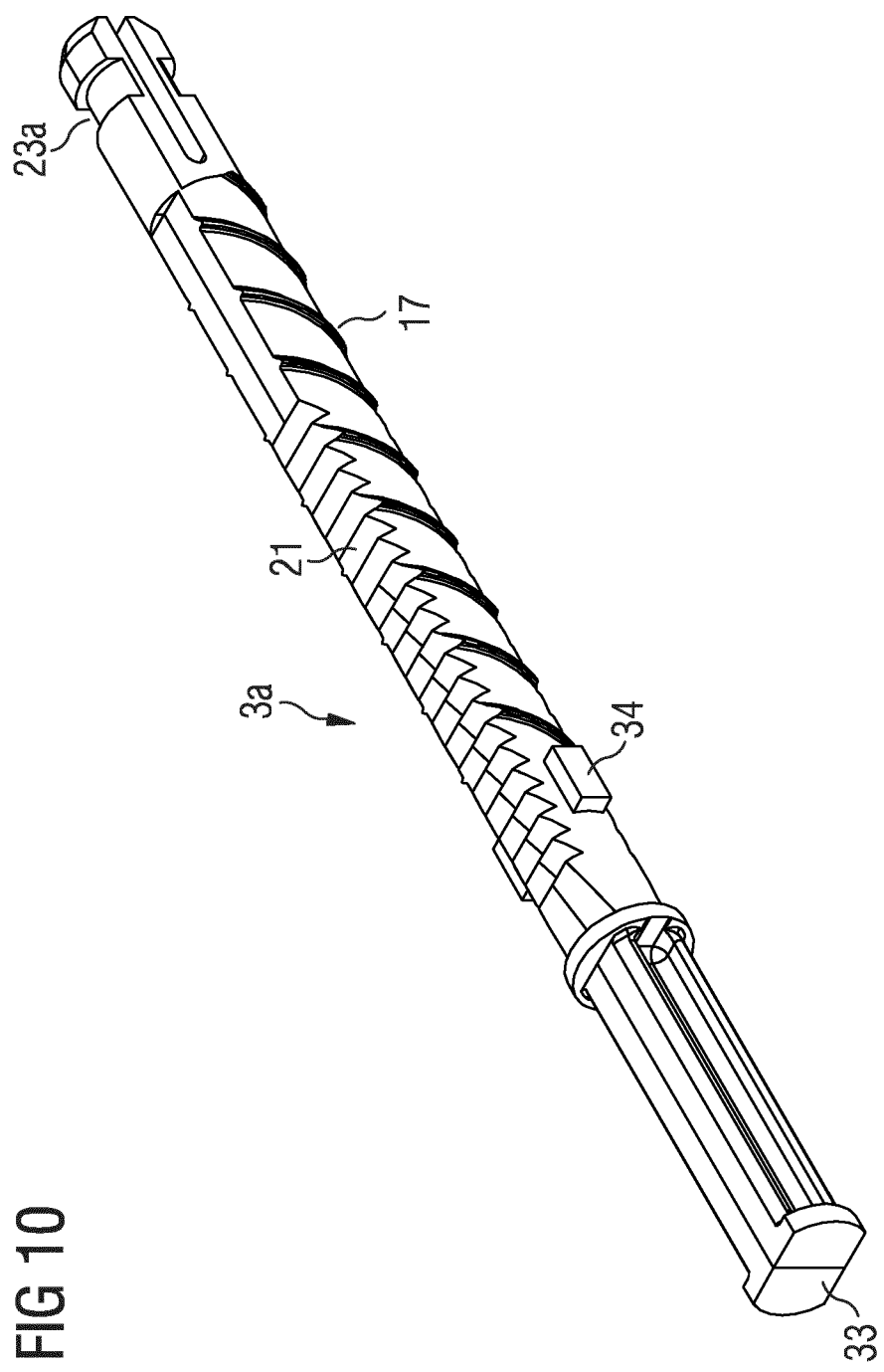

ASSEMBLY FOR A MEDICATION DELIVERY DEVICE AND MEDICATION DELIVERY DEVICE COMPRISING SUCH AN ASSEMBLY

BACKGROUND OF THE INVENTION

Field of the Invention

The present invention relates to an assembly for a medication delivery device. The present disclosure further relates to a medication delivery device. In particular, the invention relates to single-shot variable-dose medication delivery device.

Description of the Related Art

In a single-shot variable-dose medication delivery device, a dose may be displaced with respect to a body of the device in a distal direction by a piston rod. Thereby, the user settable dose of a medication may be expelled from the device. After delivery of the single dose, the device may be locked for preventing a further dose setting or dose delivery operation.

SUMMARY OF THE INVENTION

It is an object of the present invention to provide an assembly for a medication delivery device and such a medication delivery device having improved properties, e.g., increased user comfort, increased safety, lower error-proneness and/or reduced manufacturing costs.

This object may be achieved by the subject matter of the independent claims. Advantageous embodiments and refinements are subject matter of the dependent claims.

One aspect relates to an assembly for a medication delivery device. The assembly may be adapted and arranged to be integrated/to be used in a medication delivery device. This means that the assembly may provide specific structural and functional features making the assembly suitable for the medication delivery device. The medication delivery device may be a pen-type device, e.g., a pen-type injector or a pen-type pre-filled syringe. The medication delivery device may be adapted and arranged to dispense a dose, in particular exactly one dose, i.e., a single dose, of a medication. The medication delivery device may be a single-shot or single-use device. The medication may be a fluid. The single dose of the medication may be chosen or set by a user. The single dose of medication may, thus, be variable. After delivery of the single dose of the medication, the medication delivery device may be discarded. In particular, the medication delivery device may be designed such that further use of the medication delivery device for setting and dispensing a further dose of the medication may be impossible.

The assembly for the medication delivery device comprises a body. The body may constitute an outer shell of the assembly or the device. The body may be adapted and arranged to house and protect further components of the assembly or the device. The assembly comprises a piston rod. The piston rod may be an elongated component adapted and arranged to operate through the body. In particular, the piston rod can be designed to interact with a dose of a cartridge containing a medication. In this way, an axial movement of the piston rod in a distal direction may result in an axial feed of the dose, thereby expelling a predetermined amount of the medication out of the cartridge. For example, the assembly can be used in a medication delivery device comprising a cartridge holder accommodating a cartridge filled with a fluid medication, wherein a needle assembly is arranged at a distal end of the cartridge holder and being in fluid connection with the medication.

The piston rod can be manufactured as one single part or as multiple parts, for example as two parts. The piston rod is adapted and arranged to be rotated with respect to the body in a dose setting state of the assembly for setting a dose of a medication. The piston rod may be rotatable in only one direction, e.g., the counter-clockwise direction when viewing from the proximal end towards the distal end. Rotation of the piston rod in the opposite direction may be prevented. Alternatively, the piston rod can be rotatable in both directions, i.e., in the clockwise direction and in the counter-clockwise direction. The piston rod can be designed to be exclusively rotatable in the dose setting state of the assembly. In this regard, the piston rod can be prevented from any axial movement with respect to the body in the dose setting state of the assembly.

The piston rod can be axially moved in a distal direction with respect to the body in a dose delivering state of the assembly for delivering the set dose of the medication. Preferably, the assembly can be designed such that in the dose setting state of the assembly the piston rod is rotatable, thereby enabling a dose setting of a medication, and the assembly automatically switches from the dose setting state into the dose delivering state as soon as the piston rod is axially moved in the distal direction with respect to the body.

The assembly further comprises a setting nut. The setting nut is secured against rotational movement with respect to the body, but enabled for axial movement with respect to the body. This means that the setting nut is only enabled to axially travel with respect to the body. Rotation of the setting nut with respect to the body is prevented. The setting nut is helically coupled with the piston rod. This means that rotational movement of the piston rod can be transformed into helical movement of the setting nut with respect to the piston rod, i.e., a combined axial and rotational movement of the setting nut with respect to the piston rod. This in turn may finally provoke an axial movement of the setting nut with respect to the body. On the other hand, an axial movement of the piston rod can be transformed into a helical movement of the setting nut with respect to the piston rod and/or into an axial movement of the setting nut with respect to the body.

The setting nut is preferably designed for the purpose of controlling a dose setting operation in the dose setting state of the assembly. The setting nut is adapted and arranged to axially travel in the proximal direction with respect to the body for setting a dose of a medication due to a helical movement of the setting nut with respect to the piston rod when the piston rod is rotated with respect to the body in the dose setting state of the assembly. This means that due to a relative axial movement between the setting nut and the piston rod, a dose setting operation can be performed.

Additionally, the setting nut can be designed for the purpose of controlling a dose setting operation in the dose setting state of the assembly. The setting nut can be adapted and arranged to axially travel in the distal direction with respect to the body for delivering the set dose of the medication when the piston rod is axially moved in the distal direction with respect to the body in the dose delivering state of the assembly.

The setting nut can be adapted and arranged to axially travel starting from a dose setting ready position in proximal direction with respect to the body for setting a dose of a medication. The dose setting ready position can be defined by a part of the body. For example, the setting nut can abut to a part of the body, when being positioned in the dose setting ready position, the part of the body thereby defining or delimiting the dose setting ready position of the setting nut.

The assembly provides for an increased user comfort and is easy in handling. A dose setting operation can easily be performed by rotating the piston rod. Due to this, as explained above, the setting nut axially travels from a dose setting ready position in proximal direction into a predetermined dose setting end position. The axial travel path of the setting nut between the dose setting ready position and the dose setting end position, thereby, determines an allowed axial travel path of the piston rod in a subsequent dose delivering operation.

A subsequent dose delivering operation can easily be performed by axially moving the piston rod in distal direction. The piston rod can be adapted and arranged to be axially movable along the travel path determined by the axial travel path of the setting nut in the preceding dose setting state.

Preferably, the piston rod and the setting nut are directly helically coupled. This means that the assembly does not require any intermediary part between the piston rod and the setting nut. Hence, the assembly also provides for a relatively simple design and reduced manufacturing costs. This also has the advantage that movement of the piston rod can be directly transmitted to the setting nut such that an exact dose setting operation and/or dose delivering operation can be performed. This provides for an increased safety and lower error-proneness.

The term "distal" or "distal end" refers to that end of the assembly or a component or a respective device that is closest to a dispensing end of a device in which the assembly can be used. The term "proximal" or "proximal end" refers to that end of the assembly or a component or a respective device that is furthest away from the dispensing end of the device in which the assembly can be used. The term "distal direction" refers to the direction from the proximal end to the distal end of the assembly or a component or a respective device. The term "proximal direction" refers to the opposite direction, i.e., the direction from the distal end to the proximal end of the assembly or a component or a respective device.

According to one embodiment, an axial travel path of the setting nut in the proximal direction with respect to the body corresponds to the set dose of the medication. As explained above, the axial travel path of the setting nut can be defined between a dose setting ready position and a proximal end position of the setting nut. A short axial travel path of the setting nut in proximal direction may correspond to a comparatively small dose of a medication, whereas a long axial travel path of the setting nut in proximal direction may correspond to a comparatively high dose of a medication. Hence, due to an axial travel path of the setting nut, a predetermined dose of a medication can easily be set. In this way, the assembly can be suitable for variable-dose medication delivery devices.

The piston rod may provide an axial dose setting stop adapted and arranged to inhibit a further axial travel of the setting nut in the proximal direction with respect to the body. For example, the setting nut may abut the axial dose setting stop. Hence, the axial dose setting stop of the piston rod delimits a proximal end of a maximum possible axial travel path of the setting nut in the proximal direction with respect to the body. Hence, misuse of the device or malfunction of the device can be prevented. Furthermore, the axial dose setting stop can provide a mechanical end-of-range feedback to a user operating the device.

The maximum possible axial travel path of the setting nut in the proximal direction with respect to the body may correspond to a maximum settable dose of the medication. Also in this way, misuse of the device due to an erroneously too high dosage of a medication can be prevented, which means a high security feature.

According to one embodiment, the piston rod is configured to be secured against rotational movement with respect to the body in the dose delivering state of the assembly. In this regard, the piston rod can only be axially moved with respect to the body. In combination with the helical coupling of the piston rod with the setting nut, as explained above, this results in the fact that the setting nut is secured against relative movement with respect to the piston rod, when the piston rod is axially moved in the distal direction with respect to the body.

In this way, in the dose delivering state of the assembly an axial travel path of the setting nut corresponds to an axial travel path of the piston rod. In other words, an axial travel path of the setting nut is transmitted with a ratio of 1:1 to an axial travel path of the piston rod. Hence, the axial travel path of the setting nut may directly determine a stroke of medication to be expelled out of a delivery device in which the assembly may be used.

The piston rod can be secured against rotational movement with respect to the body by anti-rotation features cooperating between the piston rod and the body. For example, for this purpose the piston rod comprises protrusions or fins, whereby the body provides one or more inner tracks in which the protrusions or fins of the piston rod can be axially guided. The one or more inner tracks of the body can, for example, be designed as axially extending webs.

Due to the measures, as explained above, the piston rod can be rotatable in the dose setting state and exclusively axially movable in the dose delivering state of the assembly with respect to the body. The assembly can be designed such that, as soon as the piston rod is axially moved in distal direction, the assembly automatically switches from the dose setting state into the dose delivering state, thereby securing the piston rod against rotational movement as explained above. Hence, an unambiguous and "discrete" switching between the dose setting state and the dose delivering state can be realized. Moreover, these measures have the advantage, that in the dose delivering state, any further rotational movement of the piston rod is not possible. This may prevent an unintentional variation of a set dose and/or a further dose setting operation, after the first dosing operation has been performed.

According to one embodiment, the assembly further comprises non-return means adapted and arranged to mechanically cooperate with the piston rod and to prevent axial movement of the piston rod in the proximal direction with respect to the body in the dose setting state and/or in the dose delivering state of the assembly. The non-return means can be realised by a separate and additional component, member or sleeve arranged in the assembly, in particular in the body of the assembly. Alternatively, the non-return means can be realised by the body itself comprising a specially shaped part for providing this functionality.

Due to the non-return means, the assembly is designed as a non-resettable assembly. This means that the piston rod can only be axially moved in distal direction, but not in proximal direction. In this way, a dose delivery of a medication delivery device, in which the assembly is used, can only be performed as long as the piston rod is axially movable in distal direction. Once the piston rod has reached a predetermined distal end position with respect to the body, no further dose delivery is possible, since the piston rod cannot be moved back in proximal direction out of the distal end position with respect to the body. Hence, a dose delivery functionality realised by an axial feed of the piston rod in distal direction is connected with a maximum possible axial travel of the piston rod in distal direction with respect to the body, determined by a predetermined length along the axial dimension of the piston rod. In the case that the piston rod has axially travelled once along the full predetermined length, any further axial feed of the piston rods for a dose delivering operation is no longer possible.

In connection with the explained feature of the piston rod being enabled for rotational movement in the dose setting state and being exclusively axially movable in the dose delivering state, the non-return means can have the additional functionality to provide an assembly specially designed for a single-shot use. In this way, a dose setting operation can be performed by rotational movement of the piston rod with respect to the body in the dose setting state. For performing a dose delivering operation, the piston rod can be subsequently axially moved in distal direction with respect to the body. Once the piston rod is axially moved in distal direction, the anti-rotation features cooperating between the piston rod and the body, as explained above, prevent the piston rod from being rotationally moved with respect to the body. Hence, the assembly has switched from the dose setting state into the dose delivering state. Due to the non-return feature, as explained above, the piston rod cannot be moved in proximal direction and, therefore, the anti-rotation features between the piston rod and the body cannot be brought out of engagement anymore. In this state, the piston rod can only be further axially moved in the distal direction. Rotational movement of the piston rod or axial movement of the piston rod in proximal direction are no longer possible. In this way, no further dose setting operation is possible, once the piston rod has been axially moved in distal direction for the first time. Hence, with such a feature combination, the assembly is suitable for a variable-dose, single-shot use.

According to one embodiment, the body provides an axial end stop adapted and arranged to inhibit a further axial travel of the setting nut in the distal direction with respect to the body when the setting nut abuts the axial end stop, the axial end stop thereby delimiting a distal end of an axial travel path of the setting nut in the distal direction with respect to the body. Such an axial end stop defines a predetermined end position of the axial travel of the setting nut in the distal direction. The axial end stop can simultaneously also define a dose setting ready position of the setting nut, as explained above. This means that the dose setting nut starts its axial travel in proximal direction at a dose setting ready position and returns during a dose delivery operation to this same position, now acting as the axial end stop.

In connection with the explained feature of the piston rod being enabled for rotational movement in the dose setting state and being exclusively axially movable in the dose delivering state and with the setting nut being in the axial end stop position, a further axial movement of piston rod in the distal direction may be blocked due to a helical coupling of the setting nut with the piston rod and due to an abutment of the setting nut with the axial end stop of the body. In this way the axial end stop of the body defines an axial end stop of the piston rod with respect to the body. Hence, the axial end stop of the body automatically stops a dose delivering operation of the assembly, when the setting nut abuts the axial end stop. Since the piston rod simultaneously is secured against further rotational movement, the assembly is prevented from unintentional variation of a set dose and/or a further dose setting operation. Therefore, the assembly provides for a safe and reliable dose delivering functionality.

Additionally, in connection with the non-return feature, as explained above, a lock-out feature of the assembly can be realized. This means that the assembly is blocked against further use, when the setting nut abuts the axial end stop on the body, thereby also preventing the piston rod from further axial movement in the distal direction and simultaneously preventing the piston rod from axial movement in the proximal direction due to the non-return feature. Hence, in this state, the piston rod cannot longer be moved either in the distal direction or in the proximal direction, such that the assembly has reached a lock-out state. Further operation of the assembly then is no longer possible.

According to one embodiment, the piston rod comprises an outer thread and the setting nut comprises an inner thread for helical coupling between the piston rod and the setting nut. In this way, the setting nut can travel along the axial dimensions of the piston rod due to a helical movement with respect to the piston rod. The outer thread of the piston rod and the inner thread of the setting nut are preferably designed such that a friction between the setting nut and the piston rod is minimised. In this way a rotational movement of the piston rod can be easily transmitted into axial movement of the setting nut with respect to the body by a user. Moreover, the outer thread of the piston rod and the inner thread of the setting nut are preferably adapted to the requirements regarding the axial travel of the setting nut during the dose setting state and/or the dose delivering state as well as the requirements regarding a minimum possible dose and a maximum possible dose to be set by the assembly.

According to one embodiment, the body comprises at least one axially extending inner track for axially guiding the setting nut, and the setting nut comprises guiding means guided in the inner track of the body. The track can be defined e.g., by axially extending inner webs. The at least one inner track for axially guiding the setting nut may correspond with the at least one inner track of the body for guiding the piston rod in the dose delivering state, as explained above. Alternatively, the at least one inner track for axially guiding the setting nut may be different to the at least one inner track of the body for guiding the piston rod. The guiding means of the setting nut can be defined e.g., by lateral protrusions on the setting nut. In this way, the setting nut is rotationally splined, but axially slidable with respect to the body.

According to one embodiment, the body comprises lock means, wherein the lock means and the piston rod are configured to mechanically cooperate with each other such that, in an unprimed state of the assembly, rotational movement of the piston rod with respect to the body for performing a dose setting operation is prevented. The unprimed state corresponds to an initial state or prime lock state of the assembly. Since a rotational movement of the piston rod with respect to the body is prevented in the unprimed state, a dose setting operation cannot be performed, not to mention any dose delivering operation. The unprimed state represents a kind of security state of the assembly and may indicate to a user that the assembly has not been used yet and still is in an initial state prior to first use. Moreover, a user of a medication delivery device provided with such an assembly may rely on the fact that in the unprimed state the medication delivery device still provides the predetermined amount of medication contained in the device. It is conceivable to provide prime indication means in or on the assembly displaying the unprimed state of the assembly to a user. For using the assembly or the respective medication delivery device providing such an assembly, a user may switch the assembly from the unprimed state to the primed state by performing a predetermined user interaction. Once the assembly has been brought into the primed state, a subsequent dose setting can be performed by rotating the piston rod as explained above. In this regard, the primed state may correspond to the mentioned dose setting state. Alternatively, it is conceivable that an additional user interaction is necessary in order to switch the assembly from the primed state into the dose setting state.

The piston rod may comprise an anti-rotation member, wherein, in the unprimed state, the lock means engages the anti-rotation member in a splined manner such that rotational movement of the piston rod with respect to the body for setting the dose of the medication is prevented, and wherein for priming the medication delivery device the piston rod is axially movable in the distal direction with respect to the body such that the lock means and the anti-rotation member are brought out of engagement for enabling rotational movement of the piston rod with respect to the body for setting the dose of the medication. In this way, the assembly can be unambiguously and reliably switched from the unprimed state into the primed state, wherein a subsequent dose setting operation by rotating the piston rod can be performed. In this regard, a mentioned necessary user interaction for switching the assembly from the unprimed state into the primed state consists of an axial movement of the piston rod in the distal direction with respect to the body such that the lock means and the anti-rotation member are brought out of engagement for enabling rotational movement of the piston rod with respect to the body.

In the unprimed state of the assembly, the setting nut may be axially movable in the distal direction with respect to the body due to an axial movement of the piston rod in the distal direction with respect to the body such that the setting nut is brought from an initial position with respect to the body into a dose setting ready position with respect to the body. The dose setting ready position may define a so-called prime stop position by abutment of the setting nut with a part of the body. For example, the dose setting ready position can be the same position as defined by an axial end stop of the body (cf. above explanations in this regard). The assembly can be designed such that an initial axial movement of the piston rod in the distal direction with respect to the body for switching the assembly from the unprimed state into the primed state provokes and abutment of a front end of the piston rod with a dose of a cartridge filled with a medication, when the assembly is used in a respective medication delivery device. Due to this, an initial air gap or clearance between the piston rod and the dose can be traversed and/or any air bubble in the cartridge removed, thereby ensuring a correct subsequent dose delivery by an axial feeding movement of the piston rod pushing the dose in the cartridge in distal direction for expelling a predetermined amount of medication. Hence, a wrong dosage in a subsequent dose delivering operation can be prevented.

According to one embodiment, the piston rod comprises a piston rod front part and a piston rod rear part which are mechanically coupled. The piston rod rear part may extend out of the body in proximal direction so as to be operable by a user in the dose setting state and in the dose delivering state of the assembly. In this embodiment, the piston rod front part may be helically coupled with the setting nut. In this way, the assembly may provide an increased user comfort, wherein the user may grip the piston rod rear part for operating the piston rod during the dose setting state and/or the dose delivering state.

Preferably, the piston rod front part and the piston rod rear part are secured against rotational movement with respect to each other. This means that a rotational movement of the piston rod rear part is directly transformed into a rotational movement of the piston rod front part. Preferably, the piston rod front part and the piston rod rear part are secured against axial movement with respect to each other. This means that an axial movement of the piston rod rear part is directly transformed into an axial movement of the piston rod front part.

According to a further aspect, a medication delivery device is described. The medication delivery device may comprise the previously described assembly. The assembly may be integrated in the device or may be part of the device. The device may be a variable-dose single-shot device. The device may be supplied to the user in an unprimed state, as explained above. Before the device is in a condition for setting the single dose of the medication, the user may have to prime the device. After delivery of the single dose of the medication, the device may be locked such that a further dose setting and dose delivery operation may be prevented. In this way, a user-friendly and safe device is provided which has a low number of components.

The medication delivery device may comprises a cartridge containing a medication. The medication may be dispensed in a dose delivery operation by the assembly. Alternatively, the medication delivery device may be a syringe containing a medication. The medication may be dispensed in a dose delivery operation by the assembly.

In the following text, a set of advantageous aspects is described. The aspects are numbered to facilitate referencing features of one aspect in other aspects. Features from the aspects are not only relevant in connection with the specific aspects they relate to but are also of relevance on their own. Moreover, the features and measures as described in the following set of advantageous aspects may be taken alone or in combination with the measures and features of an assembly as explained above.

The following aspects relate to a specifically designed guiding nut for guiding a piston rod of a respective assembly for a medication delivery device, wherein the guiding nut provides first feedback means adapted and arranged to mechanically cooperate with counter means of a body of the assembly for providing audible and/or tactile feedback, when the guiding nut is rotated with respect to the body. In this way, provision of a device with high user comfort and high safety is facilitated.

1. An assembly for a medication delivery device comprising
   a body,
   a piston rod adapted and arranged to be rotated with respect to the body in a dose setting state of the assembly for setting a dose of a medication and to be axially moved in a distal direction with respect to the body in a dose delivering state of the assembly for delivering the set dose of the medication, and
   a guiding nut secured against axial movement with respect to the body, but enabled for rotational movement with respect to the body, and configured to mechanically cooperate with the piston rod,
   wherein the guiding nut is adapted and arranged to be rotated with respect to the body due to a rotational movement of the piston rod with respect to the body in the dose setting state of the assembly, and wherein the guiding nut provides first feedback means and the body provides counter means, the first feedback means and the counter means of the body being adapted and arranged to mechanically cooperate with each other for providing an audible and/or tactile feedback, when the guiding nut is rotated with respect to the body.

2. The assembly according to aspect 1, wherein the first feedback means of the guiding nut comprise at least one protrusion and the counter means arranged on the body comprise multiple indentations, wherein audible and/or tactile feedback is provided by the at least one protrusion sliding across at least one of the multiple indentations.

3. The assembly according to aspect 1 or 2, wherein the piston rod is adapted and arranged to be axially moved with respect to the guiding nut in the dose delivering state of the assembly, wherein the guiding nut provides second feedback means and the piston rod provides counter means, the second feedback means and the counter means of the piston rod being adapted and arranged to cooperate with each other for providing an audible and/or tactile feedback, when the piston rod is axially moved with respect to the guiding nut.

4. The assembly according to any of the previous aspects, wherein the piston rod comprises a plurality of ratchet teeth and the guiding nut comprises pawl means, wherein the pawl means is adapted and arranged to mechanically cooperate with the ratchet teeth to prevent axial movement of the piston rod in a proximal direction with respect to the body, but to enable axial movement of the piston rod in the distal direction with respect to the body in the dose delivering state of the assembly.

5. The assembly according to aspects 3 and 4, wherein the pawl means of the guiding nut act as the second feedback means and the ratchet teeth act as the counter means on the piston rod to provide an audible and/or tactile feedback when the piston rod is axially moved in the distal direction with respect to the guiding nut.

6. The assembly according to any of the previous aspects, wherein the guiding nut further comprises one or more dose indicating means arranged at an outer circumference of the guiding nut indicating one or more predetermined doses of a medication, and wherein the body comprises a dose indication window adapted and arranged to display one or more selected ones of the one or more dose indicating means to a user, wherein the displayed dose indicating means change with a predetermined rotation of the guiding nut due to a rotation of the piston rod in the dose setting state of the assembly.

7. The assembly according to one of the previous aspects, wherein the first feedback means of the guiding nut and the counter means of the body are adapted and arranged to mechanically cooperate with each other so as to define multiple possible discrete positions of the guiding nut with respect to the body, thereby also defining multiple possible discrete positions of the piston rod with respect to the body due to the mechanical cooperation between the guiding nut and the piston rod.

8. The assembly according to any of the previous aspects, wherein the piston rod is configured to be secured against rotational movement with respect to the body in the dose delivering state of the assembly.

9. The assembly according to aspect 8, wherein the piston rod comprises multiple anti-rotation means arranged on an outer circumference of the piston rod and wherein the body comprises at least one axially extending inner track for axially guiding one or more selected ones of the anti-rotation means of the piston rod in the dose delivering state of the assembly, thereby blocking a rotational movement of the piston rod.

10. The assembly according to the aspects 7 to 9, wherein in the dose setting state of the assembly at each of the multiple possible discrete positions one or more selected ones of the anti-rotation means of the piston rod are positioned relative to the at least one axially extending inner track of the body so as to be ready to subsequently interact with the at least one axially extending inner track of the body in the dose delivering state of the assembly.

11. The assembly according to any of the previous aspects, wherein the piston rod comprises a piston rod front part and a piston rod rear part which are mechanically coupled, wherein the piston rod rear part extends out of the body in proximal direction so as to be operable by a user in the dose setting state and in the dose delivering state of the assembly.

12. The assembly according to aspect 11, wherein the piston rod front part and the piston rod rear part are secured against rotational movement with respect to each other.

13. A medication delivery device comprising an assembly according to any of the previous aspects, wherein the device is a variable-dose single-shot device.

14. The medication delivery device according to aspect 13, wherein either the medication delivery device comprises a cartridge containing a medication or the medication delivery device is a syringe containing a medication.

Features which are described herein above and below in conjunction with different aspects or embodiments, may also apply for other aspects and embodiments. Further aspects, features and advantages of the present invention will be apparent from the following description of preferred embodiments with reference to the accompanying drawings.

BRIEF DESCRIPTION OF THE DRAWINGS

FIG. 1 schematically shows a sectional side view of a medication delivery device according to a first embodiment, FIG. 2 schematically shows a perspective view of the medication delivery device of FIG. 1, FIG. 3 schematically shows a sectional side view of parts of a medication delivery device according to a second embodiment, FIG. 4 schematically shows an exploded view of the medication delivery device of FIG. 1, FIG. 5 schematically shows a sectional side view of the medication delivery device of FIG. 1 as supplied from the manufacturer, FIG. 6 schematically shows a sectional side view of the medication delivery device of FIG. 1 after a priming operation, FIG. 7 schematically shows a sectional side view of the medication delivery device of FIG. 1 after a dose setting operation, FIG. 8 schematically shows a sectional side view of the medication delivery device of FIG. 1 after a dose delivery operation, FIG. 9A schematically shows a first perspective view of a component of the medication delivery device according to FIG. 1 or 3, FIG. 9B schematically shows a second perspective view of a component of the medication delivery device according to FIG. 1 or 3, FIG. 10 schematically shows a perspective view of a further component of the medication delivery device according to FIG. 1 or 3, FIG. 11 schematically shows a perspective view of a further component of the medication delivery device according to FIG. 1 or 3, FIG. 12 schematically shows a perspective view of a further component of the medication delivery device according to FIG. 1 or 3.

DETAILED DESCRIPTION OF THE INVENTION

Figure 4:
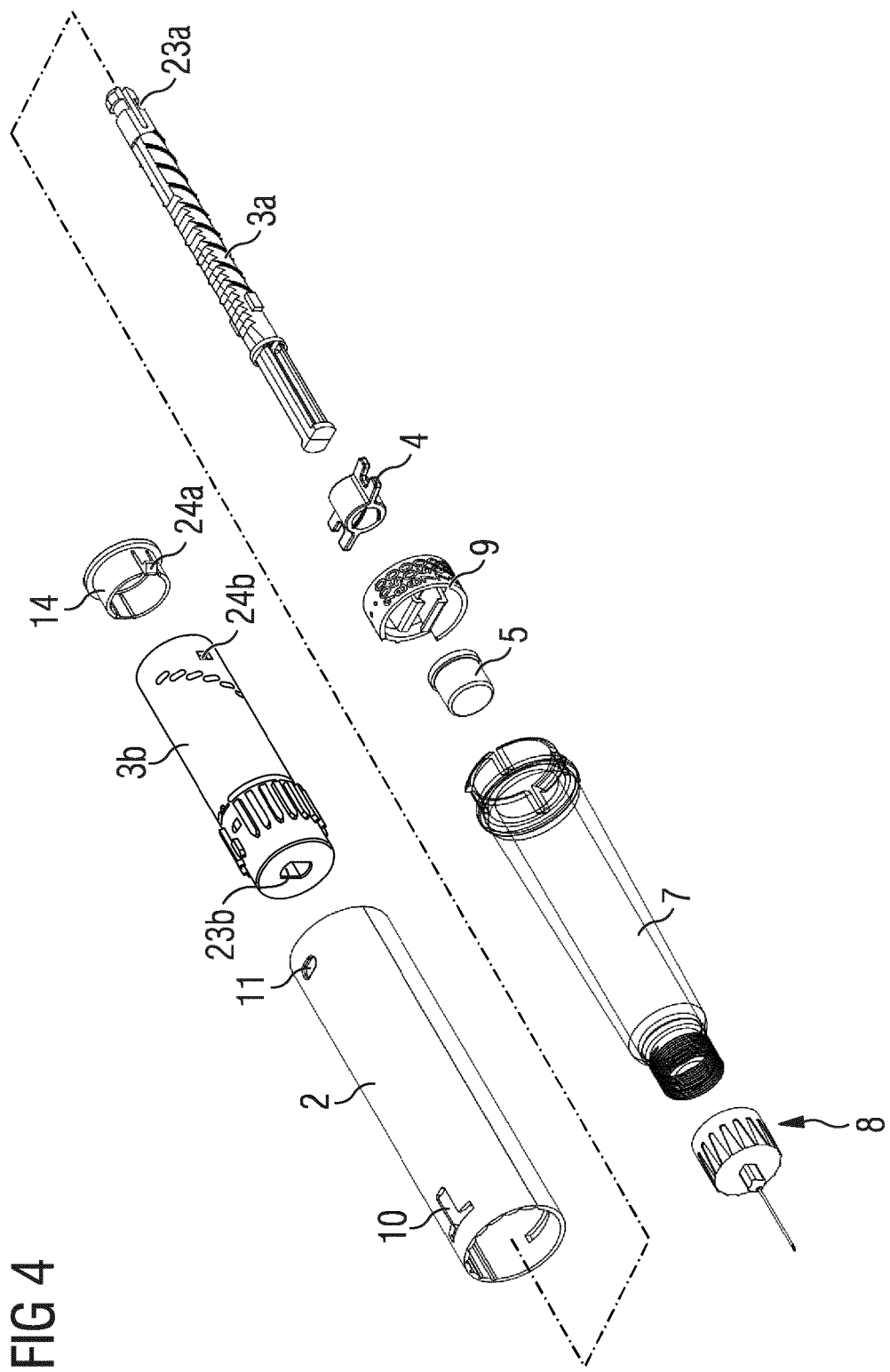

Like elements, elements of the same kind and identically acting elements may be provided with the same reference numerals in the figures.

In FIGS. 1 to 4 basic designs of a medication delivery device 1 and its components are shown. The medication delivery device 1 comprises a body 2 (see also FIGS. 9A and 9B). The body 2 may be designed to enable a safe and comfortable handling of the medication delivery device 1. The body 2 may be configured to house, fix, protect and guide inner components of the medication delivery device 1, e.g., a piston rod 3, a setting nut 4 and/or a guiding nut 9 which are described below in detail. Preferably, the body 2 limits or prevents the exposure of the inner components and/or a medication 12 to contaminants such as liquid, dirt or dust. The body 2 may be a unitary or a multipart component. The body 2 may comprise a tubular or a cylindrical shape, as shown in FIGS. 2 and 3, for example. Alternatively, the body 2 may comprise a non-tubular shape.

The medication delivery device 1 and the body 2 have a distal end and a proximal end. The distal end designates that end of the device 1 or a component thereof which is or is to be arranged closest to a dispensing end of the medication delivery device 1. The proximal end designates that end of the device 1 or a component thereof which is or is to be arranged furthest away from the dispensing end of the medication delivery device 1. In the FIGS. 1 to 8, the distal end is arranged at a needle assembly 8 of the medication delivery device 1, whereas the proximal end is arranged at an end cap 14 of the medication delivery device 1.

The medication delivery device 1 is adapted and arranged to retain a medication 12, preferably an amount provided for one maximum provided dose of the medication 12. The medication 12 is preferably a liquid. The device 1 may be a one-shot variable dose device. This means that the device 1 may be intended for a single use, i.e., for dispensing only one dose of the medication 12. After delivery of said dose of the medication 12, the device 1 may be discarded. The size of said dose of medication 12 may be settable by a user, i.e., it is a variable dose.

In one embodiment, the medication delivery device 1 comprises a cartridge 6 for holding the medication 12 (see, for example, FIG. 1). In this case, the cartridge 6 can be retained within a cartridge holder 7 (see FIG. 1). The cartridge holder 7 may be configured for stabilizing the cartridge 6 mechanically. The cartridge holder 7 may be connected to the body 2. In a further embodiment, no cartridge holder 7 may be provided and the cartridge 6 may be connected directly to the distal end of the body 2.

The cartridge holder 7 or the cartridge 6 may be non-releasably connected, e.g., snap-fitted or screwed, to the body 2. The cartridge 6 or the cartridge holder 7 may be connected to the body 2 such that relative axial and rotational movement of the cartridge 6/cartridge holder 7 and the body 2 is prevented. For this purpose, the body 2 may comprise one or more coupling members, e.g., a slot, a recess, a rib or a protrusion, and the cartridge 6 or the cartridge holder 7 may comprise one or more mating coupling members respectively.

In an alternative embodiment, the body 2 may be adapted and arranged to house and protect the medication 12. In this case, the medication 12 may be retained directly within an interior of the body 2, in particular in a specific section or region, e.g., the most distal region, of the body 2. The body 2 may be a one-piece component holding the medication 12. Accordingly, a cartridge for retaining the medication 12 and a cartridge holder may be superfluous. In this embodiment, the medication delivery device 1 is supplied and designed as a pre-filled syringe as can be gathered from FIG. 3.

The cartridge 6 or the body 2 may comprise an outlet. The medication 12 can be dispensed from the cartridge 6 or the body 2 through said outlet. A septum may seal the outlet. The septum may be made of an elastically deformable material. The device 1 further comprises a needle assembly 8. The needle assembly 8 may be connected, e.g., screwed, to the distal end of the cartridge holder 7/the cartridge 6 or the body 2 by a connecting part 8a. By means of the needle assembly 8 a needle 8b may be secured to the device 1. The septum may be pierceable by the needle 8b for dispensing the set dose of the medication 12 via the needle 8b extending through the outlet.

The medication delivery device 1 further comprises the previously mentioned piston rod 3 (see FIG. 1) or a plunger 13 (see FIG. 3). The piston rod 3 or plunger 13 may be injection moulded. The piston rod 3 or plunger 13 may be manufactured as one single part or multiple parts.

According to the embodiment as depicted in FIGS. 1, 2, 4 to 8, 10 and 11, the piston rod 3 comprises a piston rod front part 3a and a piston rod rear part 3b. The piston rod front part 3a is fixed to the piston rod rear part 3b via fixation means 23a on the piston rod front part 3a and fixation means 23b on the piston rod rear part. According to the embodiment of the piston rod front part 3a (see FIG. 10), the fixation means 23a comprise two resilient arms on the axially extending rear part of the piston rod front part 3a. According to the embodiment of the piston rod rear part 3b (see FIG. 11), the fixation means 23b comprise a through-hole with a shape corresponding to a mating shape of the axially extending rear part of the piston rod front part 3a. For example, the fixation means 23a and 23b mechanically cooperate in a snap-fitted connection. Via the fixation means 23a and 23b the piston rod front part 3a is rotationally and axially fixed relative to the piston rod rear part 3b.

Moreover, the piston rod front part 3a is helically coupled with the previously mentioned setting nut 4. In particular, the piston rod front part 3a comprises an outer thread 17 (see FIG. 10) and the setting nut 4 comprises an inner thread 44 (see FIG. 12) such that the piston rod front part 3a and the setting nut 4 are helically coupled. This means that the setting nut 4 and the piston rod front part 3a (and consequently also the setting nut 4 and the piston rod rear part 3b) may perform a combined axial and rotational movement with respect to each other.

Moreover, the piston rod front part 3a mechanically cooperates with the previously mentioned guiding nut 9 such that the guiding nut 9 rotates due to a rotational movement of the piston rod front part 3a. Moreover, the guiding nut 9 enables an axial movement of the piston rod front part 3a in distal direction, but prevents an axial movement of the piston rod front part 3a in proximal direction. The respective functionalities of the piston rod front part 3a and piston rod rear part 3b and their mechanical interaction with the setting nut 4 and the guiding nut 9 respectively are described later on in detail.

At the proximal end of the device 1, the piston rod rear part 3b is closed by an end cap 14 (see FIGS. 1, 2, and 4 in particular). The end cap 14 provides first fixation means 24a which according to the embodiment shown in FIG. 4 can be resilient cantilevers arranged as resilient wall parts of the cylindrically shaped body of the end cap 14. The piston rod rear part 3b provides second fixation means 24b which according to the embodiment shown in FIGS. 4 and 11 can be through-holes for a mating engagement with the first fixation means 24a of the end cap 14. In this way, the end cap 14 can be snap-fitted to the piston rod rear part 3b.

The piston rod 3 (or plunger 13 as depicted in the embodiment of FIG. 3) is adapted and arranged to operate through the body 2 of the device 1. The piston rod 3 (or plunger 13) is designed to transfer axial movement through the medication delivery device 1, for example for the purpose of delivering the set dose of the medication 12. The piston rod 3 (or plunger 13) is rotatable with respect to the body 2 for setting the dose of the medication 12. The piston rod 3 (or plunger 13) may be rotational in only one rotational direction, e.g., in the counter-clockwise direction when viewing from the proximal end towards the distal end.

The piston rod 3 (or plunger 13) is axially, in particular distally, moveable with respect to the body 2 for delivering the set dose of the medication 12. For dose delivery, the piston rod 3 (or plunger 13) is moved along a longitudinal axis between the distal end and the proximal end of the device 1 (as defined above). During dose delivery, rotation of the piston rod 3 (or plunger 13) with respect to the body 2 is prevented. Moreover, throughout operation of the device 1, movement of the piston rod 3 (or plunger 13) in the proximal direction is prevented. These features are described later on in detail.

The device 1 comprises a dose 5 (see FIGS. 1, 3, and 4 for example). The dose 5 may be slideably retained within the cartridge 6 or the body 2 of the device 1. Preferably, the dose 5 comprises a resilient material. The dose 5 may seal the cartridge 6 or the section of the body 2 containing the medication 12 proximally. The dose 5 is movable with respect to the cartridge 6 or the body 2. In particular, axial movement of the piston rod 3 (or plunger 13) for delivering the set dose may be transferred to the dose 5. Movement of the dose 5 in the distal direction with respect to the body 2 causes the set dose of the medication 12 to be dispensed from the device 1 through the outlet.

Figure 9A:
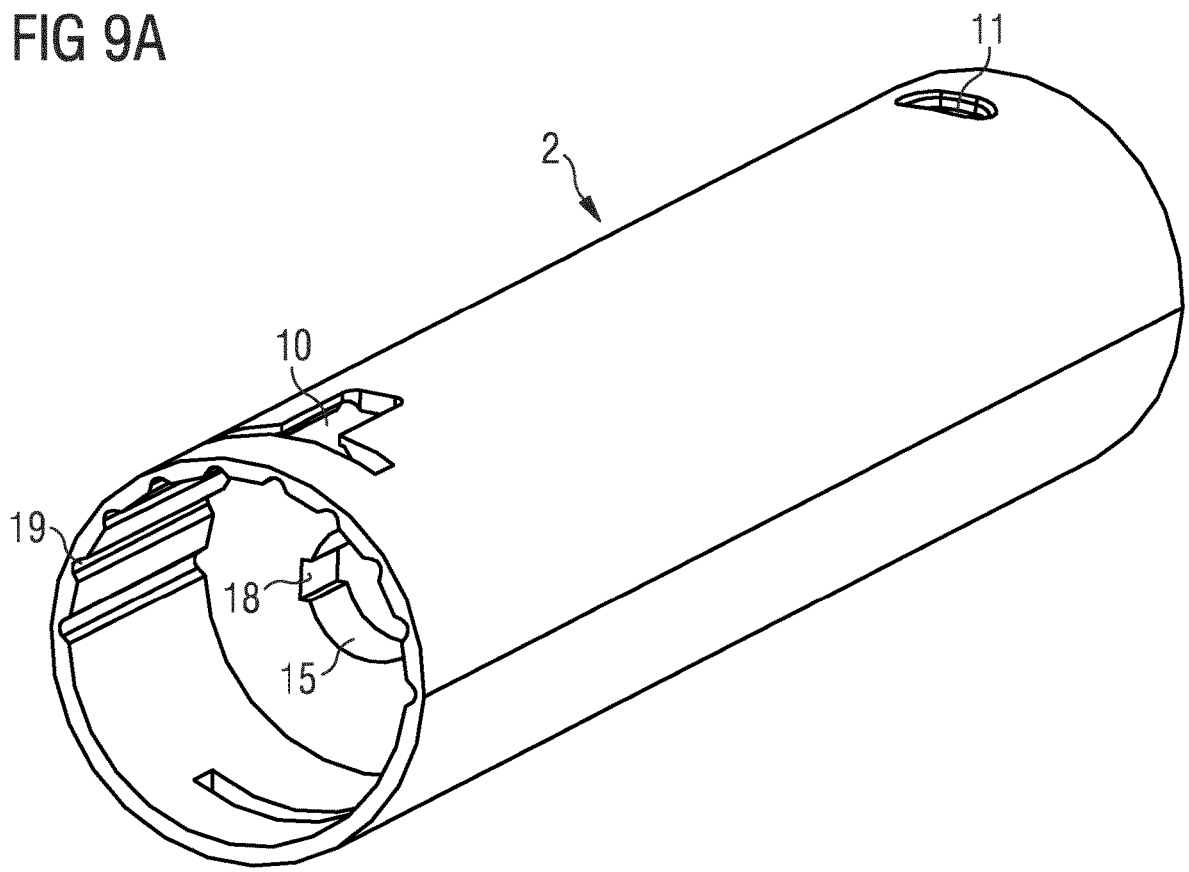

The medication delivery device 1 further provides a dose indicating window 10 and a state indicating window 11, both provided on the body 2 (see FIGS. 2, 4, and 9A). The dose indicating window 10 is provided for displaying a set dose of a medication 12. In particular, the guiding nut 9 (see FIGS. 1 and 13) provides dose indicating means (see elements 30 in FIG. 13) on its outer circumference which correspond to predetermined amounts, i.e., doses, of the medication 12. For example, the dose indicating means 30 of the guiding nut 9 can indicate units of a respective active substance within the medication 12, e.g., insulin. The functionality of the guiding nut 9 and its respective dose indicating means 30 is explained later on in detail.

The state indicating window 11 is provided for displaying a respective state of the medication delivery device 1. In particular, the piston rod rear part 3b (see FIGS. 2, 4 to 8, and 11) provides several state indicating means (see in particular elements 36 and 37 in FIG. 11) on its outer circumference which may reflect predetermined states of the device 1 to a user, when shown in the state indicating window 11. The functionality of the piston rod rear part 3b and its respective state indicating means is explained later on in detail.

In the following, assembly of the medication delivery device 1 is described in connection with FIG. 4.

In a first step, the components of the device 1 as described above are provided. These components are:
the needle assembly 8 comprising the needle 8b,
the cartridge holder 7 (containing a cartridge 6 filled with a medication 12),
the dose 5,
the guiding nut 9,
the setting nut 4,
the piston rod front part 3a,
the piston rod rear part 3b,
the end cap 14,
the body 2.

In an alternative embodiment, the piston rod front part 3a and the piston rod rear part 3b constitute one single, e.g., injection molded, component. In a further embodiment, the end cap 14 and the piston rod rear part 3b constitute one single, e.g., injection molded, component. Alternatively, the piston rod front part 3a, the piston rod rear part 3b and the end cap 14 may comprise one single, e.g., injection molded, component. For the previously mentioned alternative embodiments, the following method steps have to be adapted accordingly.

In a next step, the setting nut 4 is screwed onto the piston rod front part 3a from the rear part of the piston rod front part 3a. Screwing the setting nut 4 onto the piston rod front part 3a is possible due to the explained helical coupling between the setting nut 4 and the piston rod front part 3a.

In a next step, the end cap 14 is affixed to the piston rod rear part 3b. In particular, the end cap 14 is snap-fitted to the piston rod rear part 3b via first and second fixation means 24a and 24b.

In a next step, the piston rod front part 3a is connected to the piston rod rear part 3b with the fixation means 23a of the piston rod front part 3a mating with the fixation means 23b of the piston rod rear part 3b, such that the piston rod front part 3a and the piston rod rear part 3b are snap-fitted together and secured against relative movement with respect to each other.

Figure 9B:
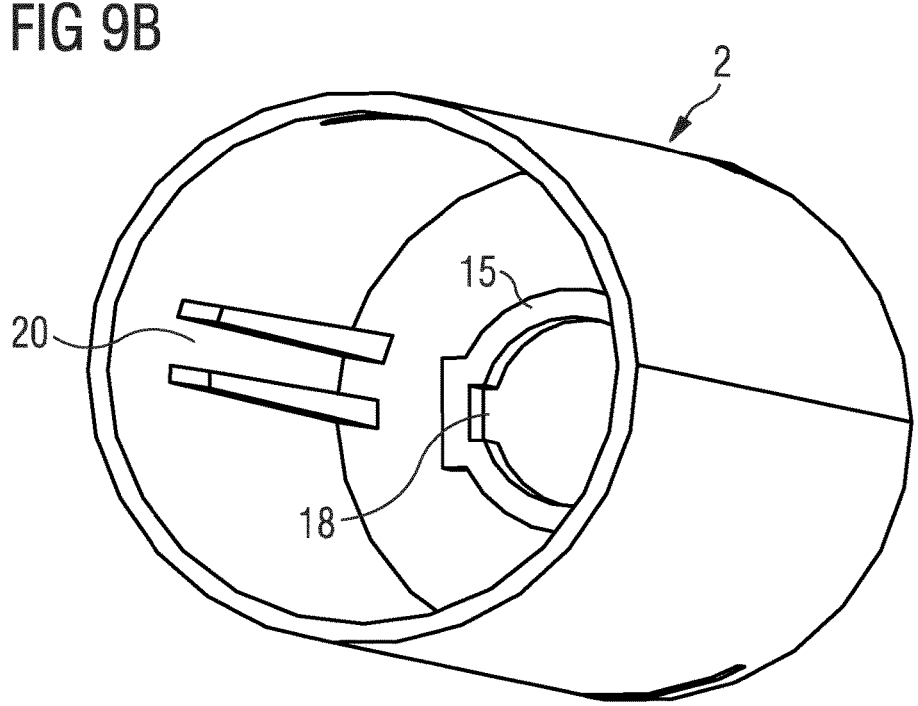

In a next step, the assembled piston rod front part 3a, setting nut 4, piston rod rear part 3b, and end cap 14 are inserted into the body 2 from its rear side as illustrated in FIG. 9B. Thereby, the piston rod front part 3a is inserted into the through-hole of the inner collar of the body 2 (see FIGS. 9A and 9B) such that the anti-rotation members 34 of the piston rod front part 3a (see FIG. 10) mate with the lock means 18 on the inner collar of the body 2 (see FIG. 9A) for splined engagement to each other. Additionally, the setting nut 4 is brought into engagement with one or more inner tracks 20 on the body 2 (see FIG. 9B). In particular, wing-like lateral protrusions 45 on the setting nut 4 are guided in the inner tracks 20 of the body 2 such that the setting nut is secured against rotational movement with respect to the body 2, but enabled for axial movement with respect to the body 2.

In a next step, the guiding nut 9 (see FIG. 13) is inserted into the body 2 from its front side as depicted in FIG. 9A. The piston rod front part 3a, thereby, penetrates the guiding nut 9 such that the guiding nut with respective pawl means 31 (see FIG. 13) jumps over a ring-shaped structure on the front end 33 of the piston rod front part 3a (see FIG. 10) and comes into engagement with the beginning of the ratchet teeth part 21 of the piston rod front part 3a. In detail, the guiding nut 9 then lies directly behind the ring-shaped structure on the front end 33 of the piston rod front part 3a, but in front of the first tooth of the ratchet teeth part 21 of the piston rod front part 3a as seen from the front end 33 of the piston rod front part 3a (see also FIGS. 5 and 10). Moreover, with the guiding nut 9 accordingly placed in the front of the body 2, a protrusion 29 on the guiding nut 9 (see FIG. 13) is brought into engagement with a respective indentation 19 on the inner circumference of the body 2 as depicted in FIG. 9A.

In a next step, the cartridge holder 7 containing the cartridge 6 may be connected to the body 2. This can be done by mechanical engagement of resilient parts of the cartridge holder 7 with respective counter means, e.g., recesses or apertures, on the body 2 such that the cartridge holder 7 can be snap-fitted to the body 2. Alternatively, the cartridge holder 7 can be mounted to the body 2 via bayonet mechanism for example. In the embodiment (see FIG. 3) where the device 1 is embodied as a pre-filled syringe, this step may be redundant. Rather, the medication 12 may be contained within the body 2 of the device 1.

Finally, the needle assembly 8 is connected, e.g., screwed, to the distal end of the device 1. The device 1 can now be supplied to the user. When supplied, the device 1 preferably is in an unprimed state and, hence, has to be primed prior to use as described below.

In the following, several operational states of the medication delivery device 1 are described in conjunction with FIGS. 5 to 8. Thereby, detailed functionalities of the involved components and parts of the device 1 are described with the aid of FIGS. 9A to 13.

Figure 5:
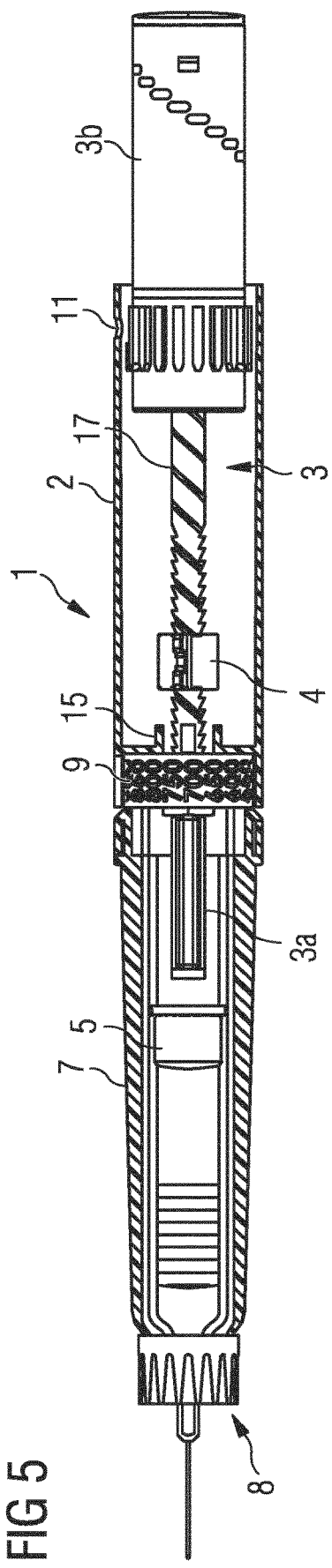

FIG. 5 schematically shows a sectional side view of the medication delivery device 1 as supplied from a manufacturer. According to the configuration of FIG. 5, the medication delivery device 1 is in a so called "unprimed state". This unprimed state reflects an initial state of the medication delivery device 1 prior to a first use. The unprimed state can be displayed to a user by a respective lock symbol 36 (see FIG. 11) which is arranged on the outer circumference of the piston rod rear part 3b. In the unprimed state, the lock symbol 36 is visible for a user through the state indicating window 11 on the body 2 (see FIGS. 5 and 9A). Hence, the user, when holding the medication delivery device 1 in his hands before its first use, may see the lock symbol 36 through the window 11.

Moreover, in the unprimed state according to FIG. 5, the piston rod front part 3a is arranged with respect to the body 2 in an initial position. In this position, there can be an air gap or a clearance between the front end of the piston rod front part 3a and the dose 5 of the cartridge 6, as exemplarily depicted in FIG. 5. The air gap may arise from manufacturing and/or assembly tolerances of components of the device 1. The size of the air gap may vary.

In the unprimed state, besides an air gap or clearance between the front end of the piston rod front part 3a and the dose 5 of the cartridge 6, there may also be air in the section of the body 2/in the cartridge 6 containing the medication 12. However, in the delivery condition, i.e., when delivering a set dose of the medication 10, an air gap between the piston rod 3 and the dose 5 and/or air in the section of the body 2/in the cartridge 6 containing the medication 12 may affect the dose accuracy, in particular for a variable dose device as described herein. More precisely, one reason which makes dose accuracy of a variable dose device so significant is that it is much more difficult to be accurate compared to a device delivering the entire contents of medication. This is because the device must perform the metering function—it cannot rely on the fill volume being accurate and then simply pushing out all of the medication. Hence, the elimination of an air gap between the piston rod 3 and the dose 5 and/or air in the section of the body 2/in the cartridge 6 become crucial in order to obtain the dose accuracy required.

For that reason, the device 1 preferably may not be operated unless a priming operation was performed by the user. In particular, in the unprimed state according to FIG. 5, a dose setting operation is prevented, since the piston rod front part 3a is rotationally fixed with respect to the body 2. This means that also the piston rod rear part 3b is rotationally secured with respect to the body 2 due to the mechanical coupling between the piston rod front part 3a and the piston rod rear part 3b as explained above. Hence, in the unprimed state the piston rod rear part 3b cannot be rotated by a user for setting a dose of the medication 12.

A mechanical interaction between the piston rod front part 3a and the body 2 can be explained regarding the FIGS. 9A and 9B in connection with FIG. 10. FIG. 10 shows the piston rod front part 3a. The piston rod front part 3a is an axially elongated rod providing a front end 33 and a rear end with the fixation means 23a for mechanical cooperation with fixation means 23b of the piston rod rear part 3b as explained above. Moreover, according to FIG. 10, the piston rod front part 3a comprises anti-rotation members 34 arranged as lateral protrusions on the piston rod front part 3a. The anti-rotation members 34 interact in the primed state according to FIG. 5 with lock means 18 on the body 2 as depicted in FIGS. 9A and 9B.

According to FIGS. 9A and 9B, the body 2 provides a collar (see also element 15 in FIG. 5) arranged in the interior of a cylindrically shaped body 2, wherein at the inner collar of body 2 the lock means 18 are formed. The lock means 18 according to FIGS. 9A and 9B are axial slits arranged to mechanically cooperate with the protrusions 34 of the piston rod front part 3a according to FIG. 10. The lock means 18 are designed so as to provide a negative shape of the anti-rotation members 34 such that the elements 18 and 34 may engage in a splined manner with each other in the unprimed state of the medication delivery device 1 according to FIG. 5 with the piston rod 3 being in its initial position with respect to the body 2. In this way the piston rod 3 is rotationally fixed with respect to the body 2.

Moreover, in the unprimed state according to FIG. 5, the setting nut 4 is located on the piston rod front part 3a in a predetermined initial position with a predetermined axial clearance to a collar 15 moulded in the interior of the body 2. The inner collar 15 provides the lock means 18 as depicted in FIGS. 9A and 9B and as described above.

Figure 6:
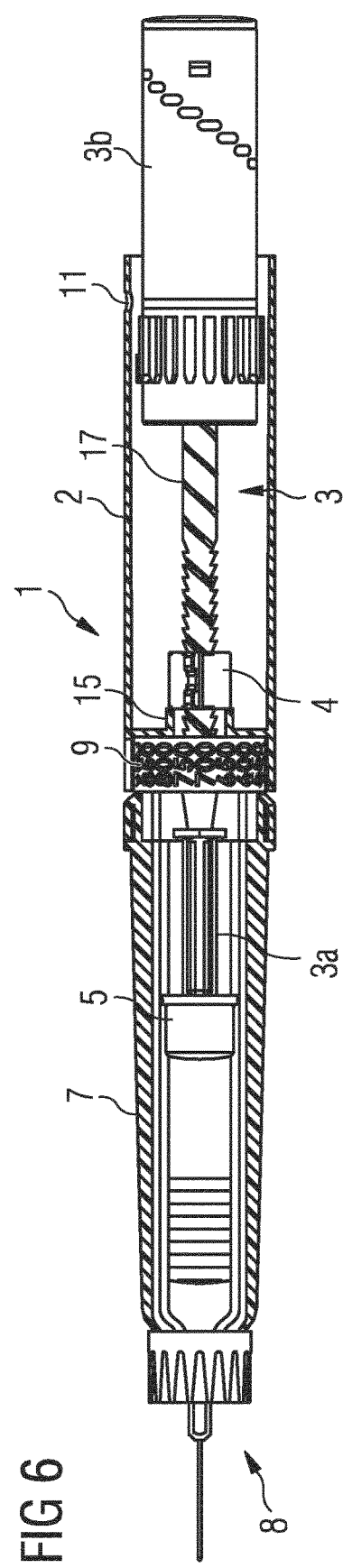
Figure 12:
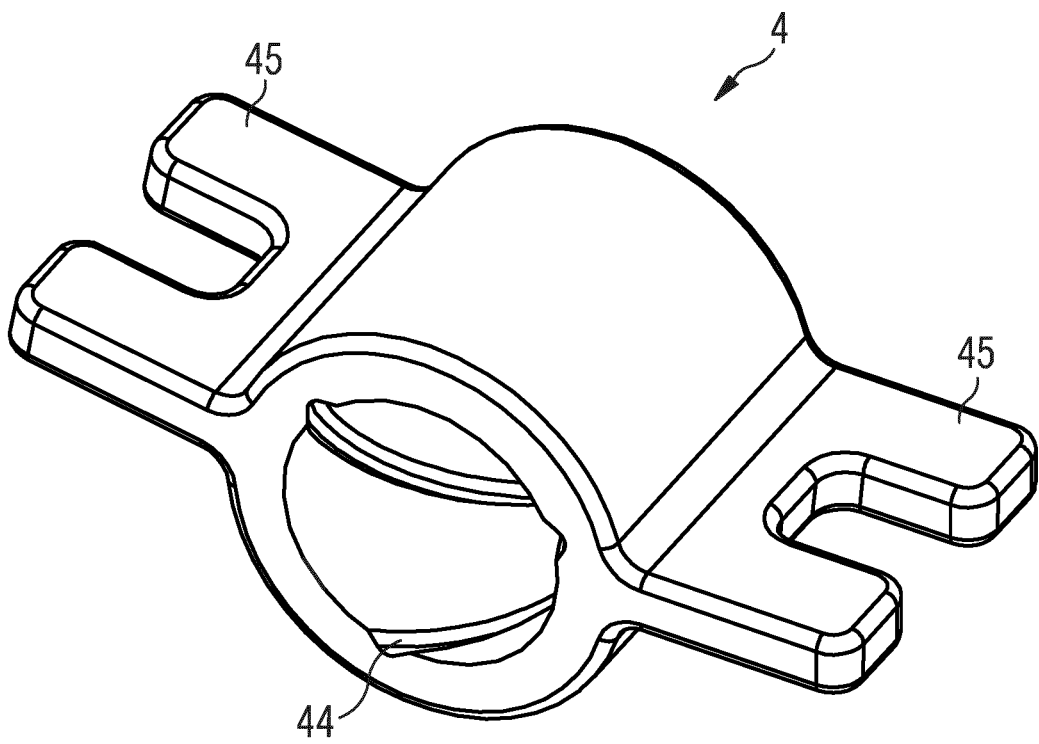

FIG. 6 schematically shows a sectional side view of the medication delivery device 1 according to FIG. 5 after a priming operation. In particular, according to FIG. 6, the piston rod 3 has been axially moved in distal direction towards the dose 5. Since the setting nut 4 is helically coupled with the piston rod front part 3a with an inner thread 44 of the setting nut 4 mechanically cooperating with an outer thread 17 of the piston rod front part 3a as explained above (see also FIGS. 10 and 12) and since in the unprimed state according to FIG. 5 the piston rod 3 is only axially movable as explained above, the setting nut 4 also axially travels in distal direction, when the piston rod 3 is axially moved in distal direction towards the dose 5. This is due to the fact that the setting nut 4 is secured against rotational movement with respect to the body 2, but enabled for axial movement with respect to the body 2. As explained above, this is achieved by guiding the setting nut 4 in axially extending tracks 20 on the interior of the body 2 as depicted in FIG. 9B. In particular, wing-like protrusions 45 laterally protruding from the setting nut 4 as depicted in FIG. 12 are guided in the axially extending tracks 20 on the body 2. In this way, a user may push the piston rod rear part 3b in distal direction and, therefore, may axially move the mechanically coupled piston rod front part 3a together with the setting nut 4 in distal direction, until the setting nut 4 abuts the collar 15 of the body 2 (see FIG. 6).

Due to an axial movement of the piston rod 3 along the axial clearance between the setting nut 4 and the collar 15 as depicted in FIG. 5, the anti-rotation members (protrusions) 34 of the piston rod front part 3a (as depicted in FIG. 10) are brought out of the splined engagement with the lock means 18 on the collar 15 of the body 2 (as depicted in FIGS. 9A and 9B and explained above) such that a rotational movement of the piston rod 3 with respect to the body 2 for subsequence setting of a dose of the medication 12 is enabled. Additionally, due to the axial travel of the piston rod 3 in the distal direction, the front end of the piston rod front part 3a abuts the dose 5 such that an air gap or clearance between the piston rod front part 3a and the dose 5 is traversed. Hence, the piston rod front part 3a is in mechanical contact with the dose 5.

Moreover, as depicted in FIG. 6, the prime indication means 36 on the piston rod rear part 3b (see FIG. 11) have also axially travelled in distal direction due to axial movement of the piston rod 3 such that in the state according to FIG. 6 now a "P" is visible through the state indicating window 11 in the body 2 for a user, instead of the initially visible lock symbol. This indicates to a user that the medication delivery device 1 according to FIG. 6 now is in a primed state and ready for dose setting.

Figure 13:
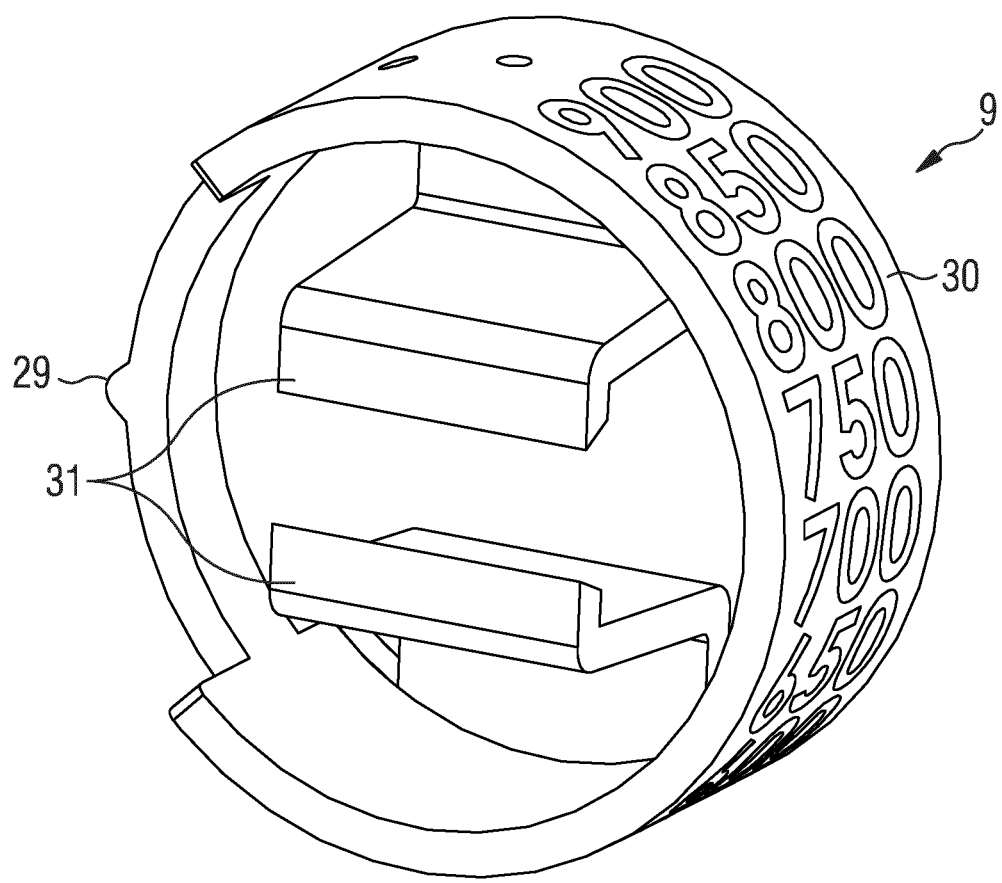
FIG. 13 schematically shows a perspective view of a further component of the medication delivery device according to FIG. 1 or 3.

Moreover, as depicted in FIG. 6 in connection with FIGS. 10 and 13, the pawl means 31 of the guiding nut 9 (see FIG. 13) mechanically cooperating with the ratchet teeth 21 of the piston rod front part 3a (see FIG. 10) have traversed the first ratchet tooth of the ratchet teeth 21 of the piston rod front part 3a due to the axial movement of the piston rod 3 in distal direction. In the primed state according to FIG. 6, the guiding nut 9, therefore, is in a snap-fit mechanical cooperation with the ratchet teeth 21 of the piston rod front part 3a according to FIG. 10. In this way, the pawl means 31 of the guiding nut 9 subsequently prevent an axial movement of the piston rod 3 in proximal direction away from the dose 5.

Since, however, the anti-rotation members 34 of the piston rod front part 3a are brought out of engagement with the corresponding lock means 18 on the body 2, as explained above, the piston rod 3 can be rotated in the primed state according to FIG. 6. For this purpose, a user may grip the piston rod rear part 3b and may rotate the piston rod rear part 3b for setting a predetermined dose, thereby also rotating the piston rod front part 3a which is mechanically coupled to the piston rod rear part 3b.

In this way, the medication delivery device 1 is in a primed state according to FIG. 6 and ready for a dose setting operation for setting a dose of a medication 12.

Figure 7:
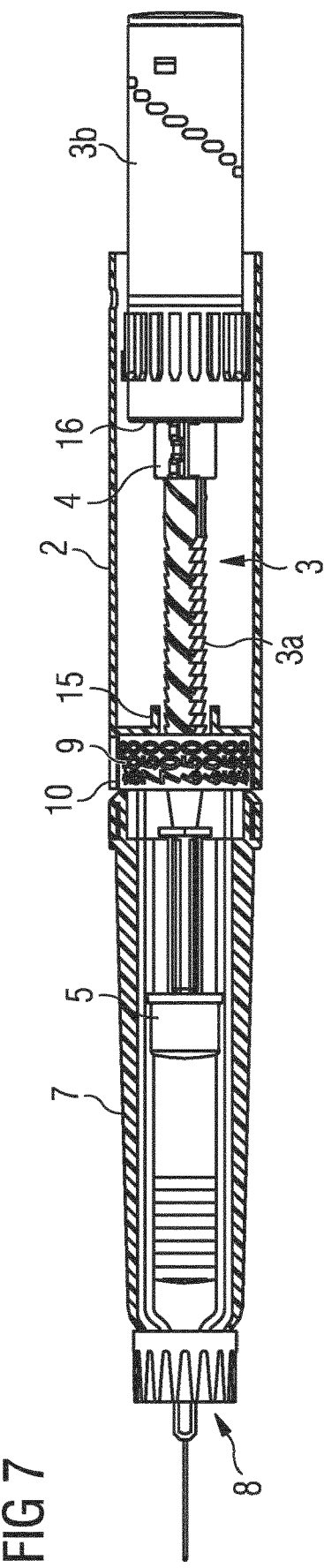

FIG. 7 schematically shows a sectional side view of the medication delivery device 1 after a dose setting operation has been performed. The state according to FIG. 7 can be achieved by rotating the piston rod rear part 3b by a user as explained above. Rotation of the piston rod rear part 3b is restricted to one predetermined rotational direction, for example the counter-clockwise direction when viewing from the proximal end towards the distal end, due to the fact, that the setting nut 4, which is helically coupled with the piston rod 3, abuts the collar 15 of the body 2 (see primed state depicted in FIG. 6). Thereby, the setting nut 4 restricts a rotational movement of the piston rod 3 only to a rotational direction that allows the setting nut 4 to axially travel in proximal direction away from the collar 15.

Provoked by a rotational movement of the piston rod 3 via the piston rod rear part 3b, the setting nut 4 axially travels in proximal direction. The piston rod rear part 3b can be further rotated by a user in the rotation direction until the setting nut 4 has axially travelled in proximal direction into a proximal end position, thereby getting in an abutment with a side wall of the piston rod rear part 3b as depicted in FIG. 7. Hence, the sidewall of the piston rod rear part 3b acts as a dose setting stop 16 inhibiting a further axial travel of the setting nut 4 in the proximal direction. In this way, the axial dose setting stop 16 of the piston rod rear part 3b delimits a proximal end of a maximum possible axial travel path of the setting nut 4 in the proximal direction with respect to the body 2. Furthermore, the axial dose setting stop 16 may provide a mechanical end-of-range feedback to a user operating the device 1.

According to FIG. 7, the setting nut 4, therefore, has travelled along the maximum possible axial travel path in proximal direction towards the piston rod rear part 3b due to the helical coupling with the piston rod front part 3a caused by a rotational movement of the piston rod rear part 3b performed by a user. In this way, FIG. 7 depicts a maximum possible set dose of a medication 12. It is clearly possible and conceivable that the setting nut 4 merely axially travels along an axial travel path in proximal direction which is shorter than the maximum possible axial travel path of the setting nut 4 depicted in FIG. 7. It is important to say that a predetermined axial travel path of the setting nut 4 corresponds to the amount of medication set in this dose setting operation. This means that a short axial travel path of the setting nut 4 in proximal direction corresponds to a comparatively small dose of medication 12, whereas a long axial travel path of the setting nut 4 in proximal direction may correspond to a comparatively high dose of a medication (a maximum possible dose is depicted in FIG. 7).

Due to a mechanical engagement between the pawl means 31 of the guiding nut 9 (see FIG. 13 and explanations above) and the piston rod front part 3a the guiding nut 9 follows a rotational movement of the piston rod 3 with respect to the body 2 during a dose setting operation performed by a user according to the above explanations. Due to a rotational movement of the guiding nut 9 with respect to the body 2 dose indication means 30 of the guiding nut 9 (see FIG. 13) also rotate with respect to the body 2 corresponding to a dose of the medication 12 set by rotating the piston rod 3 and axially travelling the setting nut 4 in proximal direction. A respectively set dose of a medication can be displayed to a user by the dose indicating window 10 in the body 2 (see FIG. 9A), thereby showing an actual dose indication means 30 on the guiding nut 9 in the dose indicating window 10. In this way, by rotating the piston rod rear part 3b, a user can read a respectively set dose of a medication in the dose indication window 10 of the body 2 due to a simultaneous rotation of the guiding nut 9 with respect to the body 2.

Furthermore, the guiding nut 9, besides the dose indication means 30, also provides the protrusion 29 arranged on the outer circumference of the guiding nut 9 as a lateral protrusion. The protrusion 29 is designed to interact with the multiple indentations 19 arranged on the inner circumference of the body 2 as depicted in FIG. 9A and explained above. In this way, during a rotational movement of the guiding nut 9, the protrusion 29 can slide across the multiple indentations 19 of the body 2, thereby providing an audible and/or tactile feedback for the user rotating the piston rod rear part 3b.

Moreover, the protrusion 21 of the guiding nut 9 and the multiple indentations 19 on the body 2 are adapted and arranged to mechanically cooperate with each other so as to define multiple possible discrete positions of the guiding nut 9 with respect to the body 2. This also defines multiple possible discrete positions of the piston rod 3 with respect to the body 2 due to the mechanical cooperation between the guiding nut 9 and the piston rod 3 via the pawl means 31 as explained above. This enables multiple fins 35 (see FIG. 11) on the outer circumference of the piston rod rear part 3b to be positioned in multiple possible discrete positions with respect to the body 2 too. In particular, due to rotational movement of the piston rod 3, the multiple fins 35 of the piston rod rear part 3b can pass the axial tracks 20 in the interior of the body 2 (see FIG. 9B), wherein at each discrete position of the piston rod 3, defined by a discrete position of the guiding nut 9 with respect to the body 2, a respective fin 35 comes into an alignment with a respective axial track 20 of the body 2. This feature is important for a subsequent dose delivering operation as explained in the following in the context of FIG. 8.

Figure 8:
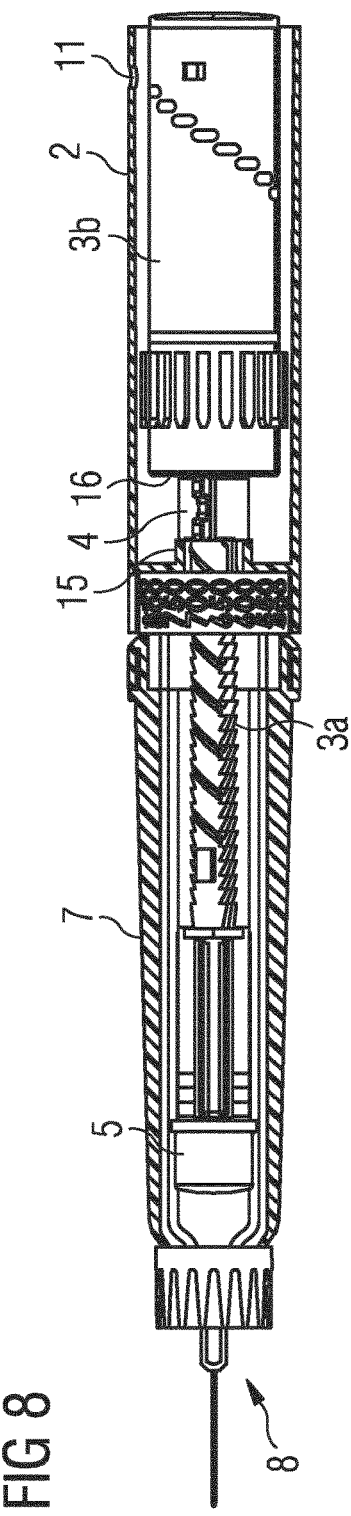

FIG. 8 schematically shows a sectional side view of the medication delivery device 1 after a dose delivery operation. In detail, starting from the state as depicted in FIG. 7, the piston rod rear part 3b has been pushed in distal direction into the body 2. This provokes an axial travel of the piston rod front part 3a likewise in distal direction, thereby pushing the dose 5 of the cartridge 6 in distal direction. In this way, the dose 5 pushes the medication 12 contained in the cartridge 6 (see FIG. 1) through the needle 8b out of the device 1.

Due to an axial travel of the piston rod 3 the setting nut 4 also axially travels in distal direction from the dose setting end position as depicted in FIG. 7 into an axial end stop position as depicted in FIG. 8. In this embodiment, the axial end stop position of the setting nut 4 corresponds to the dose setting ready position of the setting nut 4 as depicted in FIG. 6 (see above explanations). Also in the axial end stop position according to FIG. 8, the setting nut 4 abuts the collar 15 of the body 2. In this way, the setting nut 4 is sandwiched between the collar 15 and the dose setting stop 16 of the piston rod rear part 3b as explained in connection with FIG. 7.

Moreover, due to an axial travel of the piston rod front part 3a, the pawl means 31 of the guiding nut 9 are sliding across the ratchet teeth 21 on the piston rod front part 3a (see FIG. 10). In this way, the pawl means 31 in connection with the ratchet teeth 21 can provide an audible and/or tactile feedback for a user during the dose delivering operation according to FIG. 8. Additionally, since the pawl means 31 of the guiding nut 9 mechanically cooperate with the ratchet teeth 21 of the piston rod front part 3a, the guide nut 9 provides a non-return feature for the piston rod front part 3a, preventing the latter from an axial movement in proximal direction away from the dose 5. This means that the piston rod 3 can only be moved in distal direction towards the needle assembly 8 of the device 1. Hence, in this regard the device 1 is a non-resettable device.

Figure 11:
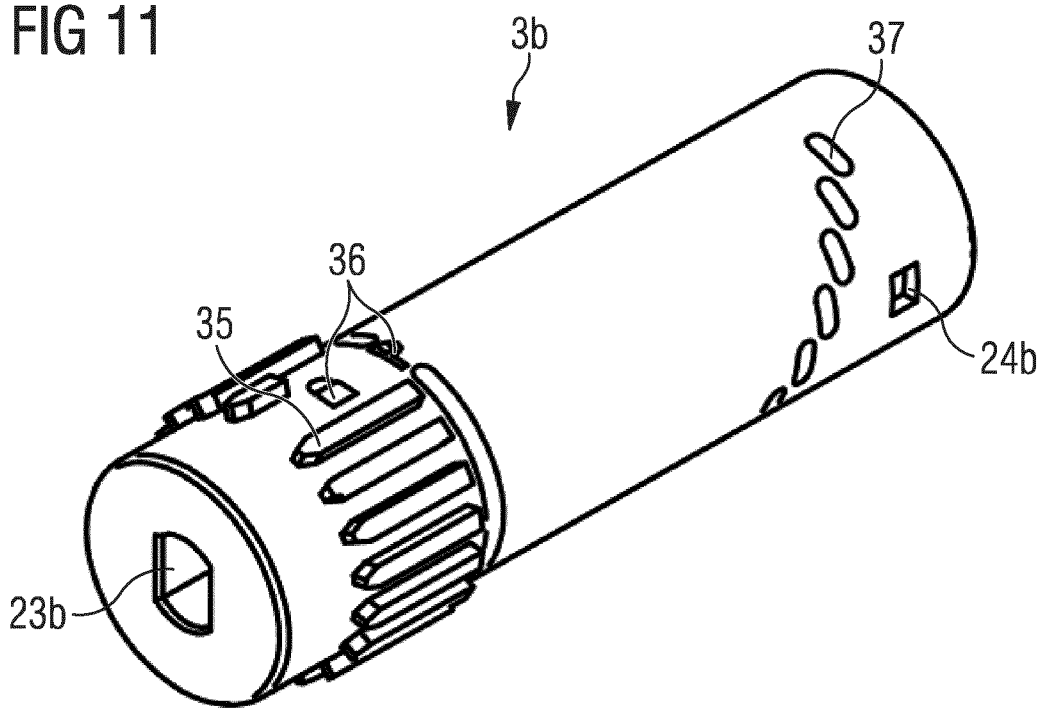

Engagement of a respective fin 35 of the piston rod rear part 3b with a corresponding axial track 20 of the body 2 can be achieved as soon as an axial movement of the piston rod 3 in distal direction is started based on the configuration shown in FIG. 7. Due to a mechanical interaction of a respective fin 35 on the outer circumference of the piston rod rear part 3b (as depicted in FIG. 11 and explained above) with a corresponding axial track 20 (see FIG. 9B and explanations above) the piston rod 3 can only be axially moved with respect to the body 2, but is secured against rotational movement with respect to the body 2.

According to FIG. 8 and due to the measures as explained above, the piston rod 3 cannot be rotated with respect to the body 2 anymore. This means that any further rotational dose setting operation is prevented. Since, furthermore, any backward movement of the piston rod 3 in proximal direction is inhibited by the pawl means 31 of the guiding nut 9, any reset operation of the piston rod 3 is prevented, too. Additionally, since the setting nut 4 abuts the collar 15 of the body 2, also a further axial movement of the piston rod 3 in distal direction with respect to the body 2 is prevented according to the configuration of FIG. 8. This means that in the state of FIG. 8, the device 1 is in an end state or so-called "lock-out" state.

This lock-out state can be displayed to a user by one of several lock-out indication means 37 arranged on the outer circumference of the piston rod rear part 3b (see FIG. 11), wherein the lock-out indication means 37 can be displayed through the state indicating window 11 in the body 2 (see FIGS. 5, 6, and 9A). Hence, a user can easily recognize that the medication delivery device 1 in the state according to FIG. 8 can no longer be operated and used.

The scope of protection is not limited to the examples given herein above. The invention is embodied in each novel characteristic and each combination of characteristics, which particularly includes every combination of any features which are disclosed herein even this combination of features is not explicitly herein.

What is claimed is:

1. An assembly for a medication delivery device comprising:
   a body,
   a piston rod adapted and arranged to be rotated with respect to the body in a dose setting state of the assembly for setting a dose of a medication and to be axially moved in a distal direction with respect to the body in a dose delivering state of the assembly for delivering the dose of the medication set, and
   a setting nut secured against rotational movement with respect to the body, axially movable with respect to the body, and helically coupled with the piston rod,
   wherein the setting nut is adapted and arranged to axially travel in the proximal direction with respect to the body for setting a dose of a medication when the piston rod is rotated with respect to the body in the dose setting state of the assembly due to being helically coupled with the piston rod,
   wherein the setting nut is adapted and arranged to axially travel in the distal direction with respect to the body for delivering the dose of the medication set when the piston rod is axially moved in the distal direction with respect to the body in the dose delivering state of the assembly, and
   further comprising fixing members on the piston rod and on the body, the fixing members engaging with each other to prevent rotational movement of the piston rod with respect to the body when the piston rod is axially moved in the distal direction with respect to the body in a dose delivering state of the assembly,
   wherein the fixing members on the body comprise one of fins and tracks, the other of the fins and tracks being on the piston rod, and wherein the fins are configured to engage in the tracks upon axial movement of the piston.

2. The assembly according to claim 1, further comprising non-return means adapted and arranged to mechanically cooperate with the piston rod and to prevent axial movement of the piston rod in the proximal direction with respect to the body in the dose setting state and/or in the dose delivering state of the assembly.

3. The assembly according to claim 1, wherein an axial travel path of the setting nut in the proximal direction with respect to the body corresponds to the set dose of the medication.

4. The assembly according to claim 1, wherein the piston rod provides an axial dose setting stop adapted and arranged to inhibit a further axial travel of the setting nut in the proximal direction with respect to the body when the setting nut abuts the axial dose setting stop, the axial dose setting stop thereby delimiting a proximal end of a maximum possible axial travel path of the setting nut in the proximal direction with respect to the body.

5. The assembly according to claim 1, wherein a maximum possible axial travel path of the setting nut in the proximal direction with respect to the body corresponds to a maximum settable dose of the medication.

6. The assembly according to claim 1, wherein the body provides an axial end stop adapted and arranged to inhibit a further axial travel of the setting nut in the distal direction with respect to the body when the setting nut abuts the axial end stop, the axial end stop thereby delimiting a distal end of an axial travel path of the setting nut in the distal direction with respect to the body.

7. The assembly according to claim 1, wherein the piston rod comprises an outer thread and the setting nut comprises an inner thread for helical coupling between the piston rod and the setting nut.

8. The assembly according to claim 1, wherein the body comprises at least one axially extending inner track for axially guiding the setting nut, and wherein the setting nut comprises guiding means guided in the inner track of the body.

9. The assembly according to claim 1, wherein the body comprises lock means, wherein the lock means and the piston rod are configured to mechanically cooperate with each other such that, in an unprimed state of the assembly, rotational movement of the piston rod with respect to the body for performing a dose setting operation is prevented.

10. The assembly according to claim 9, wherein the piston rod comprises an anti-rotation member, wherein, in the unprimed state of the assembly, the lock means engages the anti-rotation member in a splined manner such that rotational movement of the piston rod with respect to the body for setting the dose of the medication is prevented, and wherein, for priming the assembly, the piston rod is axially movable in the distal direction with respect to the body such that the lock means and the anti-rotation member are brought out of engagement for enabling rotational movement of the piston rod with respect to the body for setting the dose of the medication.

11. The assembly according to claim 10, wherein, in the unprimed state of the assembly, the setting nut is axially movable in the distal direction with respect to the body due to an axial movement of the piston rod in the distal direction with respect to the body such that the setting nut is brought into a dose setting ready position with respect to the body.

12. The assembly according to claim 1, wherein the piston rod comprises a piston rod front part and a piston rod rear part which are mechanically coupled, wherein the piston rod rear part extends out of the body in the proximal direction so as to be operable by a user in the dose setting state and in the dose delivering state of the assembly, and wherein the piston rod front part is helically coupled with the setting nut.

13. The assembly according to claim 12, wherein the piston rod front part and the piston rod rear part are secured against rotational movement with respect to each other.

14. A medication delivery device comprising an assembly according to claim 1, wherein the medication delivery device is a variable-dose single-shot device.

\* \* \* \* \*